United States Patent
Nahum et al.

(10) Patent No.: US 9,530,605 B2
(45) Date of Patent: Dec. 27, 2016

(54) LASER ACTIVATED MAGNETIC FIELD MANIPULATION OF LASER DRIVEN ION BEAMS

(71) Applicant: HIL APPLIED MEDICAL LTD., Omer (IL)

(72) Inventors: Eyal Gad Nahum, Jerusalem (IL); Shmuel Eisenmann, Tel-Aviv (IL); Arie Zigler, Rishon Le Zion (IL); Sagi Brink-Danan, Jerusalem (IL); Yiftach Katzir, Tal Shahar (IL)

(73) Assignee: HIL APPLIED MEDICAL LTD., Omer (IL)

( * ) Notice: Subject to any disclaimer, the term of this patent is extended or adjusted under 35 U.S.C. 154(b) by 0 days.

(21) Appl. No.: 14/375,204

(22) PCT Filed: Jan. 31, 2013

(86) PCT No.: PCT/IL2013/000010
§ 371 (c)(1),
(2) Date: Jul. 29, 2014

(87) PCT Pub. No.: WO2013/114351
PCT Pub. Date: Aug. 8, 2013

(65) Prior Publication Data
US 2014/0368108 A1    Dec. 18, 2014

Related U.S. Application Data

(60) Provisional application No. 61/593,033, filed on Jan. 31, 2012.

(51) Int. Cl.
*H01J 23/00* (2006.01)
*H01J 27/02* (2006.01)
(Continued)

(52) U.S. Cl.
CPC ............ *H01J 27/022* (2013.01); *G21B 3/006* (2013.01); *G21K 1/093* (2013.01); *H01J 27/18* (2013.01)

(58) Field of Classification Search
CPC ............ H05H 7/00; H05H 7/08; H05H 7/22; H05H 13/00; H05H 15/00; H01J 27/18; H01J 27/22; H05G 2/001
(Continued)

(56) References Cited

U.S. PATENT DOCUMENTS

| | | |
|---|---|---|
| 2,101,669 A | 12/1937 | Bruche et al. |
| 4,186,409 A | 1/1980 | McMullin |

(Continued)

FOREIGN PATENT DOCUMENTS

| | | |
|---|---|---|
| CN | 101088020 A | 12/2007 |
| CN | 101248505 A | 8/2008 |

(Continued)

OTHER PUBLICATIONS

PCT International Search Report and Written Opinion of the ISA, mailed Oct. 11, 2013 in PCT/IL2013/000010.

(Continued)

*Primary Examiner* — Tung X Le
(74) *Attorney, Agent, or Firm* — Daniel Feigelson; Fourth Dimension IP (57) ABSTRACT

A system for generating pulses of charged particles, comprising a high intensity pulsed laser emitting laser pulses which, when impacting a target, generate pulses of charged particles. The particles passes through an electromagnet energized by a low inductance current feed incorporating a light activated switch to turn the energizing current on and off. Part of the light of the laser pulse is directed onto the light activated switch, such that the magnetic field is optically synchronized with the generated pulses of charged (Continued)

particles. This enables energizing the magnet only during passage of the pulses, such that it is lighter and more energy efficient than prior art systems using CW electromagnets. Synchronization also enables selection of charged particles having a predetermined range of particle energy, by timing activation of the magnetic field such that it diverts onto a selected beam path only the particles having the predetermined range of energies.

19 Claims, 6 Drawing Sheets (51) Int. Cl.
*G21K 1/093* (2006.01)
*G21B 3/00* (2006.01)
*H01J 27/18* (2006.01)

(58) Field of Classification Search
USPC ............ 315/500, 505, 506; 250/396 R, 398, 250/423 R, 505; 378/122, 119, 143, 145
See application file for complete search history.

(56) References Cited

U.S. PATENT DOCUMENTS

| | | | |
|---|---|---|---|
| 4,301,362 A | 11/1981 | Mourou | |
| 5,335,258 A * | 8/1994 | Whitlock | H05G 2/001 |
| | | | 378/119 |
| 5,930,331 A | 7/1999 | Rentzepis et al. | |
| 5,952,970 A | 9/1999 | Kawahata | |
| 6,448,722 B1 | 9/2002 | Yu et al. | |
| 6,906,338 B2 | 6/2005 | Tajima | |
| 7,501,644 B2 | 3/2009 | Zani et al. | |
| 2005/0029471 A1 | 2/2005 | Kraft et al. | |
| 2008/0073590 A1* | 3/2008 | Gorrell | H01J 25/00 |
| | | | 250/493.1 |
| 2008/0298401 A1 | 12/2008 | Faure et al. | |
| 2009/0243611 A1 | 10/2009 | Holle et al. | |
| 2011/0248651 A1* | 10/2011 | Madey | H05H 7/00 |
| | | | 315/507 |

FOREIGN PATENT DOCUMENTS

| | | |
|---|---|---|
| DE | 10 2009 040457 A1 | 3/2011 |
| DE | 10 2011 052269 A1 | 3/2012 |
| WO | WO 2010070648 A1 | 6/2010 |

OTHER PUBLICATIONS

Extended European Supplementary Search Report of the European Patent Office, in corresponding European patent application No. 13744299.2, dated Aug. 19, 2015.
Luo Wei et al "Particle Selection and beam collimation system for laser-accelerated proton beam therapy", Medical Physics, AIP, Melville, NY, US. pp. 794-806.
Yogo A et al: "Development of laser-driven quasi-monoenergetic proton beam line for radiobiology", Nuclear Instruments & Methods in Physics Research, Section A: Accelerators, Spectrometers, Detectors, and Associated Equipment, vol. 653, No. 1, (Dec. 24, 2010), pp. 189-192.
Office Action dated Feb. 1, 2016 of the Chinese Patent Office in corresponding Chinese patent application No. 201380012167.3, and English translation thereof.

* cited by examiner

LASER ACTIVATED MAGNETIC FIELD MANIPULATION OF LASER DRIVEN ION BEAMS

This application is a 371 of PCT/IL2013/000010, filed Jan. 31, 2013 and claiming the benefit of U.S. Ser. No. 61/593,033, filed Jan. 31, 2012. The contents of both of these applications are incorporated herein by reference.

FIELD OF THE INVENTION

The present invention relates to the field of laser driven fast ion and charged particle beam manipulation, especially using laser activated magnetic fields.

BACKGROUND OF THE INVENTION

Fast ion beams are of interest for various applications including production of radioactive isotopes, neutron production, radiography, fusion, and various forms of radiation therapy. Beams of fast ions are typically produced in accelerators of various configurations such as cyclotrons or synchrotrons. Accelerators are relatively large and expensive machines that are costly to run and maintain.

The development of very short pulse lasers that are capable of providing extremely high intensities and electric fields, has stimulated research in exposing matter to laser light electric fields to generate therefrom fast ions. In a laser based accelerator, a high intensity laser beam is focused on a target which contains the elements of the ions that are being accelerated, the laser interacts with the target, ionizes it and accelerates the ions. A number of articles and patent documents have described such methods of using lasers to provide relatively inexpensive fast ion sources. For instance, U.S. Pat. No. 6,906,338 for "Laser driven ion accelerator" to T. Tajima describes, using laser pulses "having a pulse length between approximately 1 to 500 femtoseconds (fs)" focused to energy densities of between about $10^{18}$ to about $10^{23}$ W/cm$^2$ to produce a high flux of energetic ions such as protons, that may be used for medical purposes. The pulses are directed to interact with targets of various designs and provide radiation components that "include different species of ions (e.g., protons), x-rays, electrons, remnants of the pulse 102, and different energy components (e.g., MeV, 10's MeV, and 100's MeV within a certain energy band or window)". International Patent Application No. WO 2010/070648 for "A System for Fast Ions Generation and a Method Thereof" to some of the inventors of the present application, describes a system and method for generating a beam of fast ions. The system comprising: a target substrate having a patterned surface, a pattern comprising nanoscale pattern features oriented substantially uniformly along a common axis; and; a beam unit adapted for receiving a high power coherent electromagnetic radiation beam and focusing it onto said patterned surface of the target substrate to cause interaction between said radiation beam and said substrate, enabling creation of fast ions. Other articles are cited in the Background and General Description sections of WO 2010/070648.

Once such a high-energy beam of fast ions has been generated, it is necessary to select from it ions of the desired energy range required for the treatment to be performed using those ions, and also to direct the beam to the volume to be treated by the beam. The beam can be focused and directed by use of magnetic fields, but because of the very high magnetic fields required to divert high-energy ion beams, conventional electromagnets are extremely heavy, expensive, and require substantial energy in order to generate the required fields.

There therefore exists a need for a system and method for generating high magnetic fields for use in directing and shaping a high-energy ion beam, and for beam energy range selection, which overcomes at least some of the disadvantages of prior art systems and methods.

The disclosures of each of the publications mentioned in this section and in other sections of the specification, are hereby incorporated by reference, each in its entirety.

SUMMARY

The present disclosure describes new exemplary systems for generating streams of pulses of high energy charged particles and for manipulating those charged particles spatially or energetically using pulsed magnetic fields synchronized to the pulses of charged particles by means of optical coupling. This is termed "optical synchronization" in this disclosure. In such systems, pulses of charged particles may be generated by impacting a high intensity pulsed laser beam onto a suitable target. Since the temporal length of these pulses of charged particle is less than a picosecond, the use of a continuously energized electromagnet is disadvantageous, being very inefficient energy-wise. To take advantage of the temporal feature of the charged particles pulse, the particles pass through an electromagnet energized by a current feed incorporating a light activated switch to turn the energizing current on and off in optical synchronization with the laser pulses, and hence in synchronization with the charged particle pulses. Both the electromagnet and current feed should have very low inductance, such that the magnetic field can be switched at high speeds, in times as short as nanoseconds or hundreds or even tens of picoseconds. The current feed may advantageously be constructed in a transmission line such as a stripline, with the electromagnet itself being either a single turn, a short circuit stub on the end of the stripline or a hole on the dielectric between the strip conductors in proximity to a short circuit stub on the end of the stripline. Part of the light of the laser pulses is split off, such as by using a beam splitter, and is directed onto the light activated switch, such that the magnetic field can be switched on and off in synchronization with the laser pulses, and hence in synchronization with the generated pulses of charged particles. Since the electromagnets for generating the pulsed magnetic fields need to be energized only during the passage of the charged particles, the average power dissipation is low, such that systems of the present application are substantially smaller, lighter and more energy efficient than prior art systems using electromagnets which may need to remain energized continuously, or at least for times substantially longer than the pulse lengths.

Synchronization enables selection of charged particles having a predetermined range of particle energy, by timing activation of the magnetic field such that it is operated during the time of flight of a particle pulse through the field to divert into a selected beam path only the particles having the required range of energies. This can be achieved either by applying the magnetic field for the duration of the passage of that part of the pulse of charged particles having the desired energy range, or by applying a first magnetic field to divert pulses at the beginning of the desired energy range of particles, and a second magnetic field having an equal but oppositely directed intensity to cease the diversion of pulses at the end of the desired energy range of particles.

This implementation enables a more accurate energy selection to be achieved, as will be expounded further hereinbelow.

There is thus provided in accordance with an exemplary implementation of the devices described in this disclosure, a system for generating pulses of charged particles, comprising:

(i) a pulsed laser source, emitting laser pulses, (ii) a target adapted to generate the pulses of charged particles when impacted by the laser pulses, (iii) a current feed assembly adapted to supply current to at least one electromagnet positioned such that its magnetic field directs at least part of at least one pulse of the charged particles, the current feed incorporating a light activated switch which enables current to flow to the at least one electromagnet when illumination falls thereon, and (iv) a control system adapted to direct illumination obtained from the laser pulses onto the light activated switch, such that the electromagnet is energized in synchronization with generation of the pulses of charged particles.

In such a system, the current feed may comprise a stripline comprising a pair of parallel disposed strips of conductor separated by a dielectric material. Additionally, the electromagnet may comprises either a single loop connected to the current feed or a short circuit stub at the end of the current feed, or an aperture formed in the dielectric material in proximity to a short circuit stub at the end of the stripline.

Additional implementations can include a system as described above, in which the magnetic field is adapted to direct the at least part of at least one of the pulses of charged particles by any one of scanning, deflecting or focusing a beam of the charged particles.

The at least part of at least one pulse of the charged particles may comprise either the whole of the at least one pulse or it may be a part having a preselected range of particle energy. In the latter case, the control system should be configured to direct illumination obtained from the laser pulses onto the light activated switch only when the at least one part of the at least one pulse having the preselected range of particle energy traverses the electromagnet. Furthermore, the electromagnet should be positioned at such a distance from the target that the energy dispersion of the particles in the at least one pulse is sufficient that the preselected range of particle energy can be resolved temporally by the response time of the current feed assembly and the at least one electromagnet.

Finally, in any of the above described systems, the control system may comprise an optical delay element adapted to control the time at which the illumination obtained from the laser pulses is applied to the light activated switch.

Another exemplary implementation can involve a method of generating pulses of charged particles, comprising:

(i) projecting laser pulses onto a target adapted to generate the pulses of charged particles when impacted by the laser pulses, (ii) generating a pulsed magnetic field by means of an electromagnet energized by a current, the electromagnet being positioned to direct at least part of at least one pulse of the charged particles, (iii) switching the current by means of a light activated switch, and (iv) illuminating the light activated switch with light obtained from the laser pulses, such that the pulsed magnetic field is actuated in synchronization with generation of the pulses of charged particles.

In such a method, the directing of the at least part of at least one pulse of charged particles may comprise any one of scanning, diverting or focusing a beam of the charged particles. Furthermore, the pulsed magnetic field may be activated to direct the whole of the at least one pulse of the charged particles, or it may be activated to direct at least one part of the at least one pulse of the charged particles. In the latter case, the at least one part of the at least one pulse of the charged particles may be a part having the preselected range of particle energy, and the pulsed magnetic field may then direct particles having the preselected range of particle energy away from other particles in the at least one pulse. In any of these methods, the pulsed magnetic field should be activated during that portion of the at least one laser pulse predetermined such that the pulsed magnetic field diverts the part of the at least one pulse having the preselected range of particle energy.

Still other example implementations involve an energy selection system for a pulse of charged particles generated by impact of a laser pulse on a target, the system comprising:

(i) a current source including a light activated switch activated by light from the laser pulse, (ii) at least one electromagnet fed by the current source, generating a magnetic field switchable in synchronization with the laser pulse, the at least one electromagnet being disposed such that when energized, the charged particles are diverted from their original path, and (iii) a control system configured to activate the magnetic field during a predetermined time period adapted to divert that part of the pulse of charged particles which comprises particles of the energy range to be selected.

In such an energy selection system, the at least one electromagnet should be disposed at such a distance from the target that the energy dispersion of the particles in the at least one pulse is sufficient that particles of the energy range to be selected, can be resolved temporally by the control system.

In either of these systems, the control system may be configured to activate the at least one electromagnet from the beginning of the predetermined time period to the end of the predetermined time period, such that the predetermined time period is defined by the presence of the magnetic field. In any of these systems, the control system may incorporate an optical variable delay line.

Yet other implementations perform a method of selecting charged particles having a predetermined energy range, from a pulse of charged particles generated by impact of a laser pulse on a target, the method comprising:

(i) supplying current from an optically switched source to at least one electromagnet generating a magnetic field disposed such that when activated, the charged particles are diverted from their original path, and (ii) switching the at least one magnetic field in synchronization with the laser pulse for a predetermined time period, such that that part of the pulse of charged particles comprising particles of the energy range to be selected, is diverted by the at least one magnetic field.

In this method, the magnetic field should be disposed at a distance from the target such that the energy dispersion of the particles in the at least one pulse is sufficient that particles of the energy range to be selected, can be resolved temporally. Furthermore, the at least one magnetic field may be activated from the beginning of the predetermined time period to the end of the predetermined time period. In any of these methods, the predetermined time period may be selected by use of a variable optical delay line.

An alternative energy selection system, for selecting charged particles having a predetermined range of energies from a pulse of charged particles, may comprise:

(i) a first and a second electromagnet, each generating a magnetic field switchable in synchronization with the laser pulse, the first and second electromagnets being disposed in mutual proximity and in a position such that when energized, the charged particles are diverted from their original path, and (ii) a control system configured to activate the first electromagnet to generate a first predetermined magnetic field at a time when particles at one end of the range of energies traverses the first electromagnet, and to activate the second electromagnet to generate a magnetic field having the same intensity but of opposite sign as the first predetermined magnetic field, at a time when particles at the other end of the range of energies traverses the second electromagnet. In such a system, the pulse of charged particles may optionally be generated by impact of a laser pulse on a target, and the magnetic fields may be switched by optical control on the currents to the electromagnets.

Finally, an alternative method of selecting charged particles having a predetermined range of energies, from a pulse of charged particles, may comprise:

(i) supplying a first and a second magnetic field disposed in mutual proximity and in a position such that when activated, the charged particles are diverted from their original path, (ii) activating the first magnetic field at a time when particles at one end of the range of energies traverses the first magnetic field, and (iii) activating the second magnetic field at a time when particles at the other end of the range of energies traverses the second magnetic field, wherein the first and the second magnetic field have essentially equal intensities but opposite sign. In this method, the pulse of charged particles may optionally be generated by impact of a laser pulse on a target, and the magnetic fields may be switched by optical control on the currents activating the first and second magnetic fields.

Though the exemplary systems and methods described in this disclosure relate particularly to laser-based particle accelerators and for application in radiation therapy, especially by streams of protons, it is to be understood that these implementations are not intended to limit such systems and methods, and that other sources and other uses are also intended to be covered by this disclosure.

BRIEF DESCRIPTION OF THE DRAWINGS

The present invention will be understood and appreciated more fully from the following detailed description, taken in conjunction with the drawings in which.

DETAILED DESCRIPTION

Figure 1:
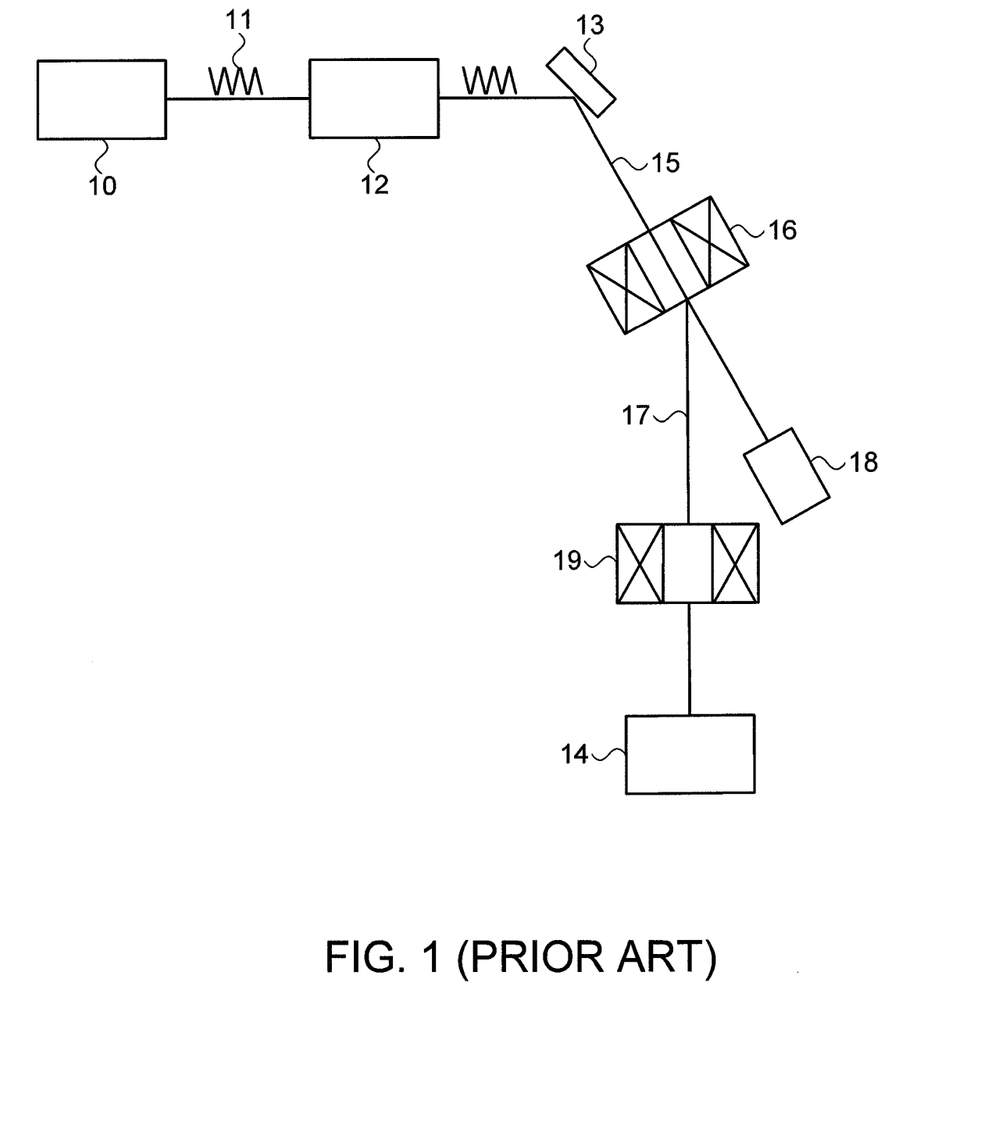
FIG. 1 shows schematically a prior art laser-based high-energy beam generating system.
Figure 2:
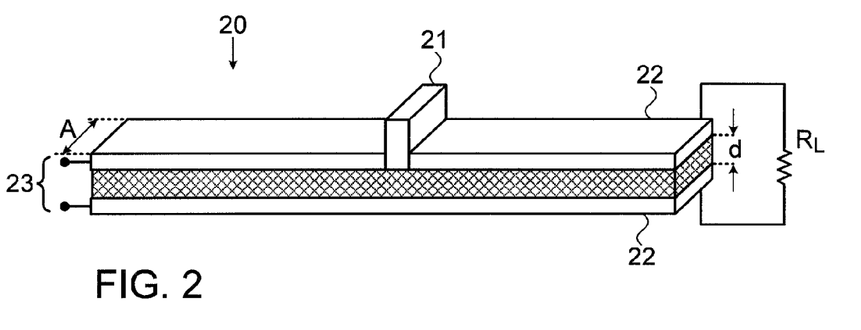
FIG. 2 illustrates schematically a current feed system in the form of a parallel strip configuration incorporating a light-activated switch, for use in providing a current pulse for generating short-pulsed high magnetic fields.

Reference is now made to FIG. 1, which illustrates schematically a prior art laser-based high-energy beam generating system such as that described in the above-mentioned U.S. Pat. No. 6,906,338. A very short pulse, high peak power laser 10 directs pulses 11 of laser light through a beam steering system 12 onto the target 13, which is selected to generate a stream of high energy ionized particles 15, which may contain a spectrum of different types of particles and having different energies. The specific type of particle and the energy desired are selected by means of one or more magnets 16 which divert the specific energetic particles required in a beam 17 towards the treatment area 14, while allowing unwanted particles and energies to be absorbed in a beam dump 18. An additional magnets or magnets 19 may be used for focusing the beam onto the target area 14, where it may be used for the treatment of tumors or other medical or industrial applications. In addition, beam slits, polarizers, collimators and other beam steering components not shown in FIG. 1, may be used. In such prior art systems, the magnets 16, 19, are generally electromagnets with copper coils. Such electromagnets are large, expensive and energy consuming Reference is now made to FIG. 2, which illustrates schematically a current feed system 20 in the form of a parallel strip configuration incorporating a light-activated switch 21, for use in providing a current pulse for generating short-pulsed high magnetic fields. As will be shown hereinbelow, such a short pulsed magnetic field will be used in the exemplary systems and methods of the present disclosure, in order to provide efficient beam manipulation for a laser powered fast ion or other charged particle beam generator. The feed system comprises a pair of low inductance conductors 22, spaced a distance d apart, and each of width A. The power source is applied at terminals 23, and the line is terminated by a matching impedance $R_L$ at its remote end 24. A dielectric material 24 is disposed between the strips, to enable application of a higher input voltage 23 without danger of breakdown. The light activated switch 21 can be a silicon Photoconductive Semiconductor Switch (PCSS), as are known in the art, such as described in U.S. Pat. No. 4,301,362 to G. Mourou for "Light activated solid state switch" and referenced cited therein, and in U.S. Pat. No. 4,186,409 to P. G. McMullin for "Light activated silicon switch". When illuminated by laser light of the appropriate wavelength, having a photon energy at least as high as the band gap energy of the semiconductor used in the device, such a PCSS can be used for switching high voltages (up to the order of 100 kV) and high currents (up to a few kA) in a very short time span, typically of the order of nanoseconds.

Figure 3:
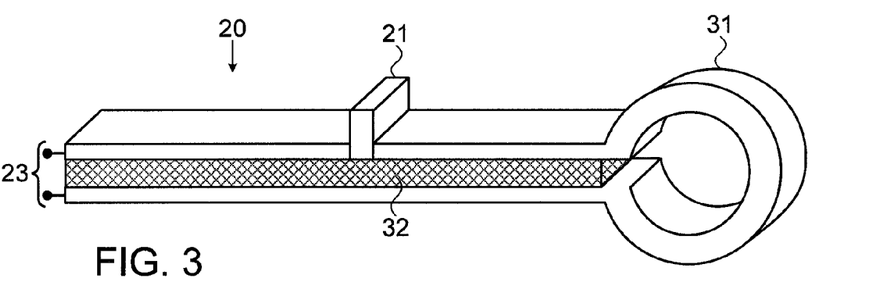
FIGS. 3 and 4 illustrate alternative electromagnets enabling the high current pulse generated using the current feed of FIG. 2 to generate the desired magnetic field pulses.

Reference is now made to FIG. 3, which illustrates one method by which the high current pulse can be used to generate the desired magnetic field pulses. A current loop 31 is used as the termination of the current feed system 20. By selecting the appropriate geometry of the current loop 31, very high magnetic field pulses can be produced within the loop 31.

Figure 4:
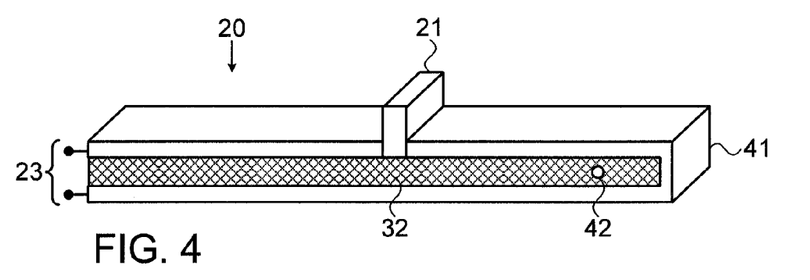

Reference is now made to FIG. 4, which illustrates another method by which the high current pulse can be used to generate the desired magnetic field pulses. In FIG. 3, the stripline current feed is terminated at a short 41, and the desired magnetic field pulse is generated within a hole 42 drilled in the high dielectric material of the strip line. Such a configuration generally has a more limited volume than that of FIG. 2, but the magnetic fields attainable can be higher.

FIGS. 3 and 4 are understood to be only two possible geometric implementations by which high magnetic field pulses can be produced from the high current pulses, and are not intended to limit this disclosure in any way. Any alternative magnetic field generating geometry may equally well be used. Furthermore, these options can be expanded by positioning two such magnets to produce a dipole field, four to produce a quadrupole, or any other desired field geometry.

Now if such a stripline current source providing typically 10 kV and 10 kA were to be operated at CW, the power required would be extremely high, reaching 100 kW. Such an electromagnet would be extremely costly because of the amount of copper involved, and extremely heavy and voluminous. However by operating the source as a pulsed source with a low to moderate repetition rates (1-10,000 Hz), and pulse widths of the order of nanoseconds, all of which is possible using currently available PCSS's, a pulsed magnetic field can be obtained using an acceptably low average power dissipation.

As an example, at a 1 kHz repetition rate, using V=10 kV and I=10 kA, only 1 kilowatt of average power is required to provide magnetic field pulses of 10 nsec. duration.

Figure 5:
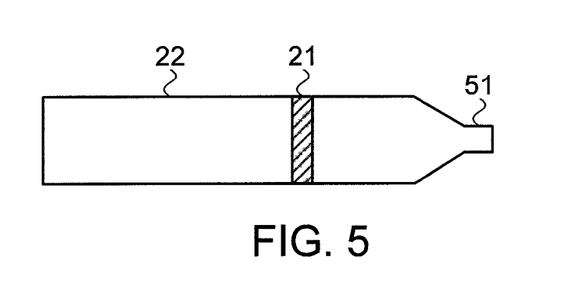
FIGS. 5 and 6 illustrate schematically methods by which the current density in the electromagnets of FIGS. 3 and 4 can be increased over that flowing in the stripline feed and the optically activated switch.
Figure 6:
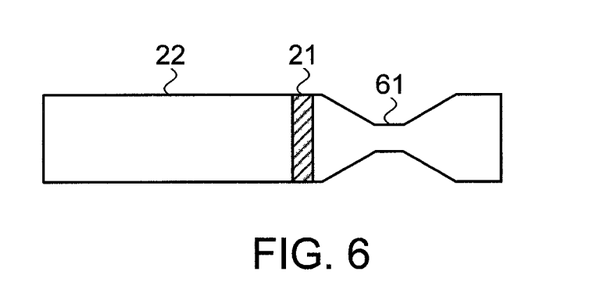

Reference is now made to FIGS. 5 and 6, which illustrate schematically, practical methods by which the required current can be delivered efficiently to the small electromagnet coil. FIG. 5 is a top view of the loop arrangement shown in FIG. 3, while FIG. 6 is a top view of the drilled hole arrangement shown in FIG. 4. At the region where the magnetic field is to be generated, the strip width A is reduced such that the current density increases. The increase is inversely proportional to the ratio of width reduction. This width reduction is shown in location 51 in FIG. 5 and in location 61 in FIG. 6. The other items have the same delineation as in the previous drawings. This geometry is advantageous since it allows a large area stripline to be used, with concomitant lower current density and inductance, while generating the magnetic field in a suitably small volume for manipulating the charged particle beam.

Figure 7:
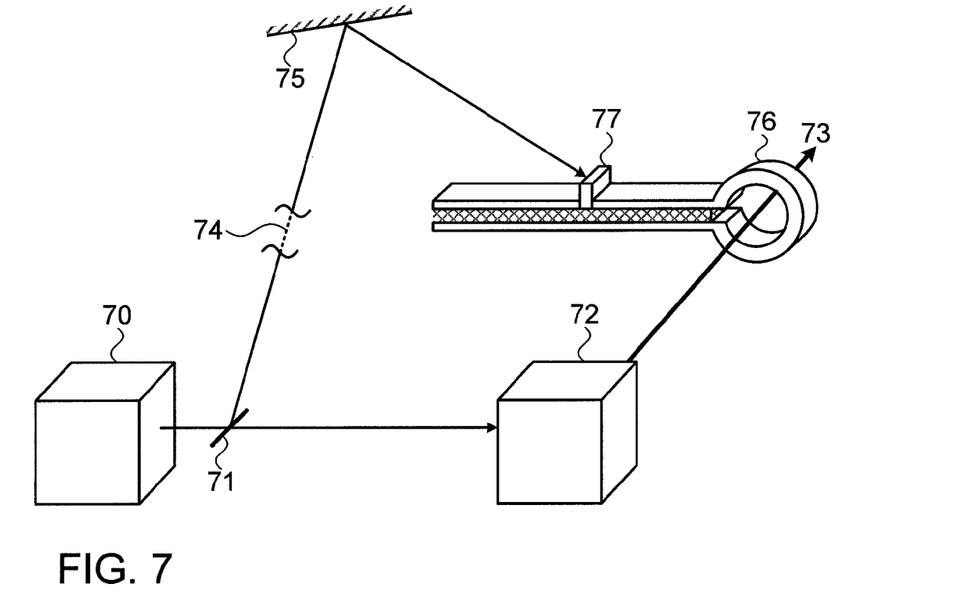
FIG. 7 illustrates schematically a laser-powered, charged particle generation system, incorporating synchronization of a pulsed magnetic field with the laser pulse.

Reference is now made to FIG. 7, which illustrates schematically a laser-powered, charged particle generation system, in which synchronization of a pulsed magnetic field with the laser pulse enables substantial savings of energy and decreased system volume.

Charged particles, such as protons, are generated and accelerated at the focal region of a high intensity laser when it radiates on a suitable target, such as a foil, gas jet, nano-structured material. The laser may be a high peak power laser in the Terawatt or even Petawatt range, which can typically be a $CO_2$, a Ti:Sapphire, a Nd:Glass laser, or a combination of these lasers. Usually such proton pulses have a temporal width of well below a nanosecond, depending on the pulse duration of the accelerating laser pulse. Although the exemplary system of FIG. 7 can be used for generation of a number of different types of charged particles or ions, the system and its different aspects will be described hereinbelow in terms of proton beam production, though it is to be understood that this is not intended to limit the application in any way.

Use of the high current sources shown in FIGS. 2 to 6 hereinabove, enable very short pulsed magnetic fields to be produced. Since the timing of the magnetic fields is determined by the opening of the optically actuated PCSS component, use of an activating optical signal extracted from the laser pulse enables the magnetic field pulse to be readily synchronized with the pulse of charged particles produced by the laser. In FIG. 7, the pulsed optical beam from the pulsed laser 70, is shown impinging on a beam splitter 71, which reflects a part of the pulsed optical beam into an optical path optionally incorporating a controlled delay line 74, which could be implemented either by using free space propagation, or propagation in a fiber. This beam is called the gating beam, and is used for gating the PCSS light activated switch 77 in the pulsed magnetic field generator. This field generator is shown in FIG. 7 as the type having a low inductance coil 76. Meanwhile the main pulsed laser beam continues to the interaction chamber 72, where the high-energy charged particle stream is generated for manipulation by the pulsed magnetic field generated in the coil 76. After manipulation or energy selection the charged particle beam is directed to the treatment area 73. In addition to a beam splitter, other options are available for providing the magnetic field synchronizing pulse, such as splitting one of the pumping lasers, using unused reflections from the compressor (zero order reflections from gratings), using the fundamental frequency left from a harmonic generator, and others. In addition it should be noted that such a pulsed magnetic field can also be synchronized with charged particle bursts produced by other means, such as synchrotrons, cyclotrons, synchro-cyclotrons and others.

In order to be used for practical applications, charged particles accelerated by a high intensity laser or any other method need to be collected, focused and/or collimated and steered towards the desired application area. In radiation therapy, for example, the desired application area is the tumor site to be treated. In some cases, the charged particle beam may even need to be aimed at a specific segment within the tumor and scanned by means of a method called Pencil Beam Scanning, where a narrow proton beam is steered inside the tumor volume which is "painted" voxel by voxel.

Moreover, many therapeutic treatments require protons having a specific energy spectrum. If the energy spectrum of the generated proton beam is not narrow enough for the requirements of the specific treatment, protons of the desired energy need to be extracted from the initial beam by being transferred through an energy selection system (ESS), which may constitute some type of magnetic analyzer or some other configuration.

Figure 8:
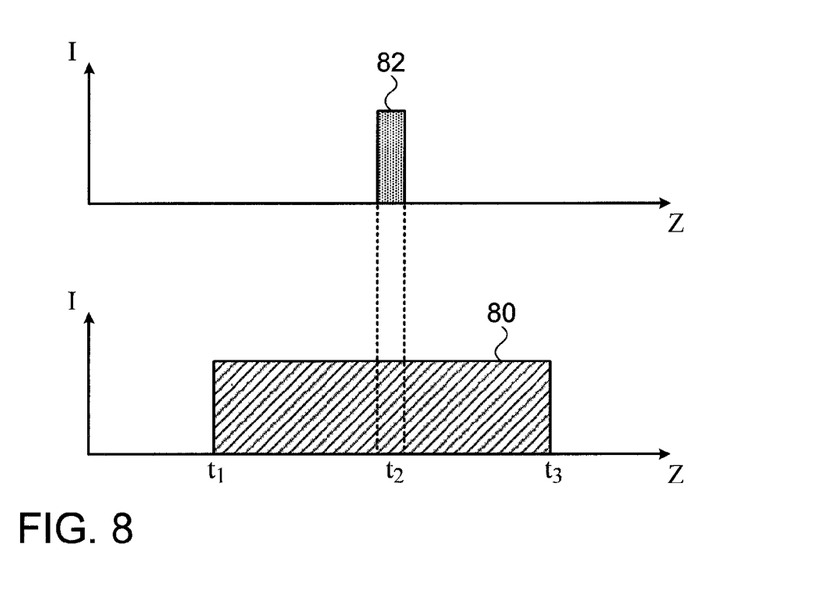
FIG. 8 illustrates schematically in graphic form, how magnetic field synchronization can be used in a novel energy selection system.

Reference is now made to FIG. 8, which illustrates schematically in a graphic form, how magnetic field synchronization can be used in a novel energy selection system. In FIG. 8, there is shown a schematic view of the intensity of the protons in a proton bunch 80 propagating along the path Z from the point of generation at the target. Since this is a "snapshot" of the propagating protons, it can also be considered to show the time plot of the intensity of the protons at a predetermined point along their propagation path. The protons all begin their flight from the target at essentially the same time, commensurate with the pulse length of the laser. Because protons of different energies propagate at different speeds, there will be spatial dispersion along the path of the proton propagation, and protons of different energies will reach the region where the magnetic field is applied to the beam at different times. This is seen in the bottom graph of FIG. 8, where the bunch of propagating protons 80 is marked with the time t of passing a predetermined point in their path z. The proton energies extend from the fastest protons at the front of the bunch, which pass the predetermined point at a time $t_3$, to the slowest protons at the end of the bunch, which pass the predetermined point at time $t_1$.

The energy spread of protons generated by means of high intensity laser impact on a target is very large, typically running from 10% to 100% of the maximum energy. Because of the ability to time the exact application of the magnetic field relative to the point in time of generation and hence also time of flight of the proton bunch, by turning on the magnetic field at the preselected time $t_2$, only the protons with the desired energy at $t_2$ are affected by the magnetic field, being diverted towards the treatment area, while all faster and slower protons continue unaffected. This is shown in the top trace of FIG. 8, where a narrow band 82 of proton energies has been selected for use in the treatment area. Typically, at a distance ranging from 1-5 m from the originating target, application of a pulse of the magnetic field for a time of 10-200 psec will result in a resolution of selection of proton energies of few percent of the total range of energies emitted. Such a method, as a stand-alone deflector or in parallel with a magnetic analyzer/2B/4B/ or other system, can thus be used as an energy selection system (ESS). Since the delay between proton pulse and the magnetic pulse can be controlled with very high precision, typically to better than 1 picosecond, and the rise time of the magnetic pulse is also very fast, this system enables the selection for manipulation of only those protons having the desired energy.

Figure 9:
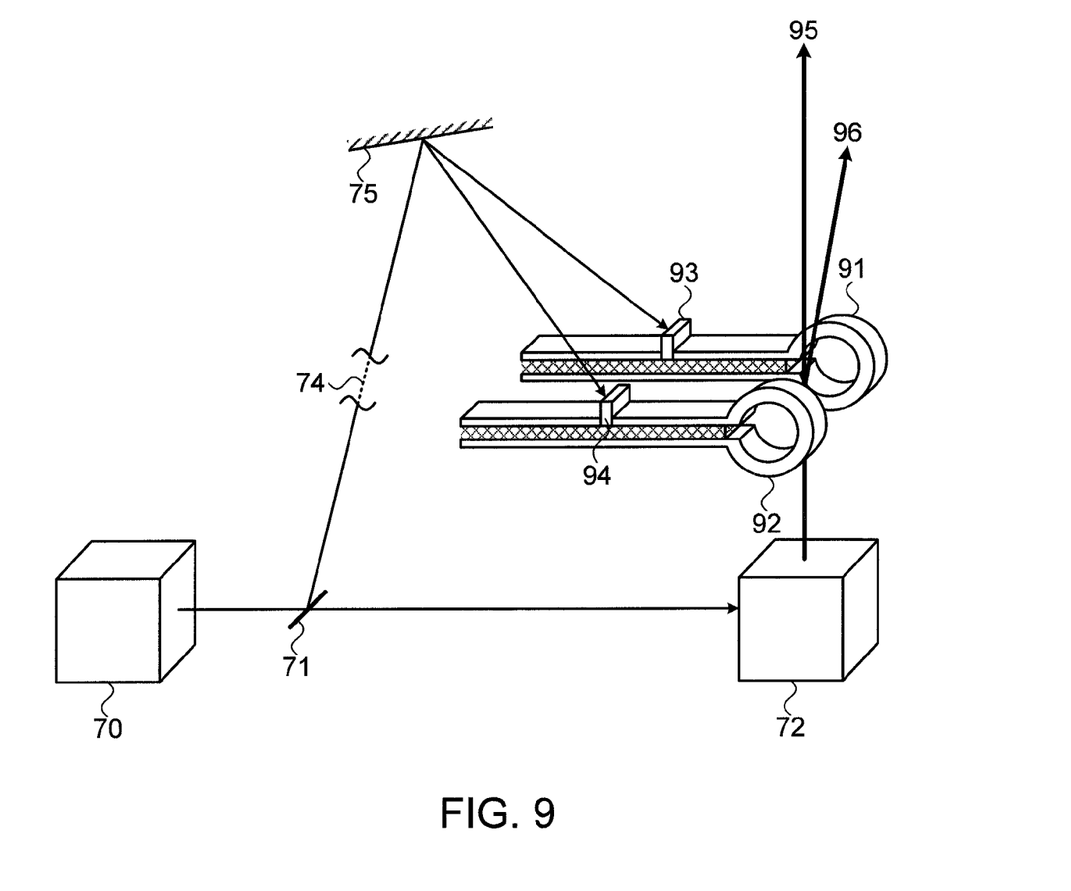
FIG. 9 illustrates schematically a laser-powered, charged particle generation system, for implementing the particle energy selection method illustrated in FIG. 8.

Reference is now made to FIG. 9, which illustrates schematically a laser-powered, charged particle generation system, similar to that shown in FIG. 7, but in which the pulsed magnetic field in synchronization with the laser pulse is used in an energy selection system, as per the method illustrated in FIG. 8. The various components of the system common to those of FIG. 7 are commonly designated. In the implementation of FIG. 8, a pair of electromagnet coils 91, 92 are used, arranged so that the particle beam 95 passes in a direction perpendicular to the magnetic field generated between the coils 91, 92. In this geometry, when the light activated switches 93, 94 are closed, the beam path 95 is deflected by the magnetic field to the direction 96, where the deflection direction is determined by the level of the magnetic field, and the particle energy. The timing of the closing of the switches 93, 94, is adjusted by the control system of the adjustable delay line 74 so that the deflecting magnetic field 91, 92, operates at the exact temporal position during the passage of the energy dispersed bunch of charged particles, so that the particles of desired energy are deflected into the output beam 96, for application in the treatment area. The non selected particles can be allowed to enter a beam dump situated in the direction of the undiverted beam 95.

However, the simple configuration shown in FIGS. 8 and 9 may not the most efficient way of energy selection, for two main reasons. In the first place, because of the very short switching times involved and the resonant nature of the low inductance electromagnet and stripline current feed circuits, although the switch-on time of the magnetic field pulse can be very short having a risetime of down to a few picoseconds, it is more difficult to turn the current off at the end of the required period during the proton bunch traverse through the field. There is a tendency of an oscillatory current to continue to flow after switch-off of the light activated switches because of the resonant nature of the circuit, and because of reflections back from the stripline into the magnet coils.

Furthermore, there is a practical problem with the implementation of the method of FIGS. 8 and 9, at least for use with proton beams. Typical energies use for treatment of tumors, which is a common use of such proton beams, range from approximately 70 to 230 MeV for typically used body tissue penetration levels of from 5 to 32 cm. However, the speed of the protons in this range of energies is very high, reaching about two thirds the speed of light for 230 MeV protons. A minimum energy range resolution of 1 MeV is optimally required in order to, for instance, perform a slice by slice scan of a tumor, each slice of a typically a few millimeters requiring an increment of a few MeV to overcome the increased absorption depth. However, in order to adequately spatially disperse a proton bunch of this range of energies, so as to be able to select an energy range of the order of 1 Mev with the magnetic pulse widths achievable in this method, it is necessary to allow the bunch to travel a distance of at least several meters from the source target. Such a long distance is impractical, and makes the entire installation unwieldy. Because of both of these limitations, a more efficient way of energy selection would be useful.

Figure 10:
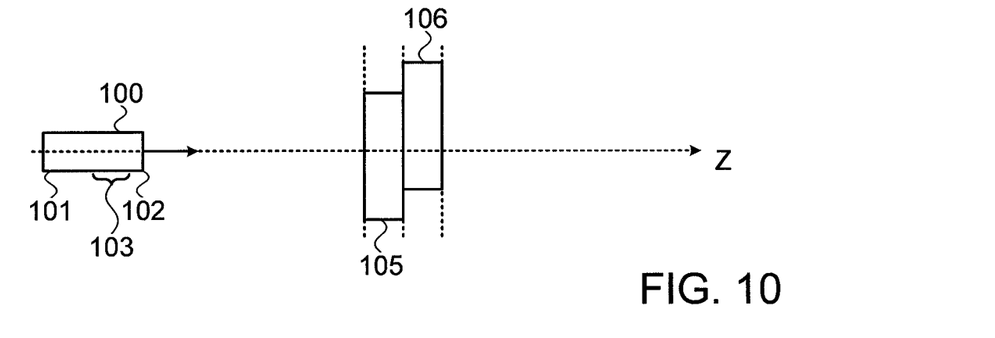
FIG. 10 illustrates an alternative way of using magnetic field synchronization to select particle energy, in which the leading edge of magnetic field pulses is used to define the proton energy spread selected by the device.

Since the rise time of the magnetic field can be as short as the order of a few picoseconds, a more efficient way of using the magnetic field synchronization to select energy is shown in FIG. 10, in which the leading edges of magnetic field pulses are used to define the proton energy spread selected by the device. In this configuration, the point in time at which the protons are selected is defined by application of the magnetic field in a first magnet at the moment in time when it is desired to commence manipulation of the protons in the selected energy band, followed by application of the magnetic field in a second magnet in the reverse direction at the moment in time when it is desired to terminate manipulation of the protons at the other end of the selected energy band. In FIG. 10, the proton bunch 100, with its dispersed range of proton energies, ranging from the slowest protons 101 at the end of the bunch, to the fastest protons 102 at the head of the bunch, is shown moving along its path z. The desired proton energy band is designated by the bracketed section 103 of the dispersed proton bunch. Two high speed magnet coils 105, 106, typically of the type described hereinabove, are located at the point of selection of the proton energy, the second coil 106, being close to the first 105 and laterally offset from the first.

Figure 11:
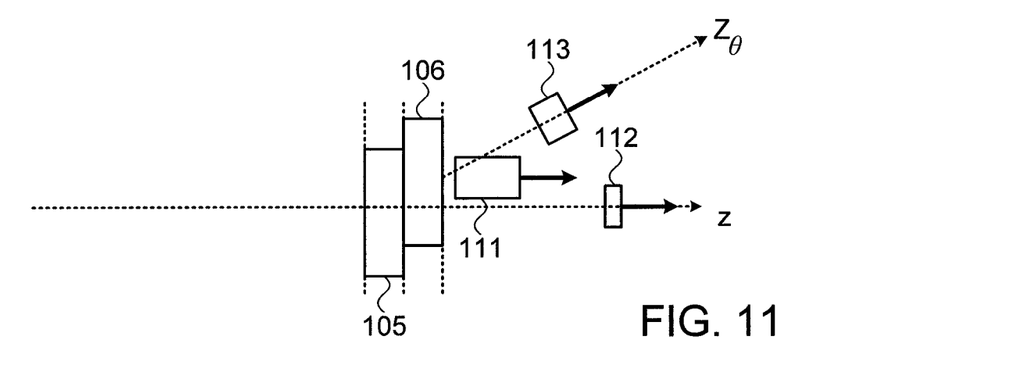
FIG. 11 shows schematically the proton selection process of FIG. 10, as implemented in practice by the magnetic fields.

Reference is now made to FIG. 11, which shows the proton selection process, as implemented by the magnetic fields in magnets 105 and 106. When no magnetic field is applied, the proton bunch continues along its original path z, as shown by the fastest proton 112. At the moment the field in the first magnet 105 is applied, the protons from that point of time on are diverted along a path $z_\theta$ at an angle $\theta$ from their original trajectory z. When selection of the desired energy spectrum of protons has been completed, a second magnetic field is applied to coil 106, the second field having the same field intensity as the first field but of opposite sign, such that it cancels out the first magnetic field from coil 105. The net magnetic field operating on the proton bunch thus returns essentially to zero, and from that point of time onwards, the protons, as designated by the proton group 111, continue on their original undiverted path z. Once this selection procedure has been completed, both magnetic fields can be allowed to fall to zero. The advantage of this form of angular and temporal selection is that reliance can be made on the very fast risetime of the magnetic fields, achievable by use of current feeds and field generating geometries such as those shown in FIGS. 2 to 6 hereinabove. Thus, the initial beam diversion time can be determined to within the few picoseconds of the first field risetime, and the end of the beam diversion can also be determined to within the few picoseconds of the second field risetime. The range of energies thus selected can be much more closely controlled than in the system shown in FIG. 8 hereinabove.

Figure 12:
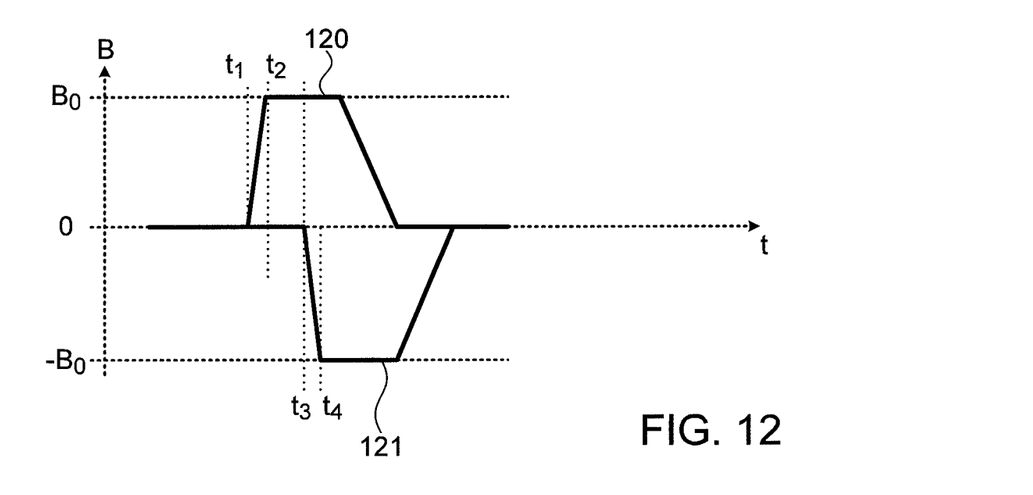
FIG. 12 is a temporal plot of applied magnetic field as a function of time for the Energy Selection System implementations of FIGS. 10 and 11.

Reference is now made to FIG. 12, which is a temporal plot of applied magnetic field as a function of time for the ESS implementation of FIGS. 10 and 11. The positive trace 120 shows the first field going up to a field intensity of $+B_0$, at which level, the protons are directed at an angle θ from their original trajectory. The first field $+B_0$ is applied at time $t_1$, and the risetime of this field is given by the period $t_2-t_1$. The negative trace 121 shows the second field $-B_0$ applied at time $t_3$, and the risetime of this field is given by $t_4-t_3$. The time ΔT during which the net field $+B_0$ is applied to the dispersing proton bunch is thus given by $$\Delta T = t_3 - t_2 \quad (1)$$

As previously mentioned, since the risetime of the fields can be made so fast, typically a few picoseconds out of a pulse selection time of a few hundred picoseconds, $$t_2 - t_1 = t_4 - t_3 << \Delta T \quad (2)$$

It should be noted that the fields do not need to be synchronized in their fall to zero, since any net field other than the level $+B_0$ will not result in the proton beam being directed at the desired angle θ from their original trajectory, which is the angle at which protons having the required energy are selected for use in the treatment area.

One disadvantage of prior at systems using cyclotrons, for instance, is that they generate a large level of neutrons. Neutrons are produced whenever a fast proton beam of energy above the activation level—approximately 10 MeV—hits a target. In such prior art systems, the energy of the cyclotron is controlled by use of double wedges inserted into the beam to absorb protons. A general advantage of use of the time-of-flight energy selection configurations shown in this disclosure, as described in FIGS. 8 to 12 hereinabove, is that they result in substantially lower levels of neutron generation than such prior art cyclotron systems. In the presently described configurations, the unselected protons are all directed along a single path, where a well shielded beam dump can be positioned far away, and no other beam absorbers need be used.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A method of generating pulses of charged particles, comprising:
    projecting laser pulses onto a target adapted to generate said pulses of charged particles when impacted by said laser pulses;
    generating a pulsed magnetic field by means of an electromagnet energized by a current, said electromagnet being positioned to direct at least part of at least one pulse of said charged particles;
    switching said current by means of a light activated switch; and
    illuminating said light activated switch with light obtained from said laser pulses, such that said pulsed magnetic field is actuated in synchronization with generation of said pulses of charged particles.

2. A method according to claim 1, wherein said directing of said at least part of at least one pulse of charged particles comprises any one of scanning, diverting or focusing a beam of said charged particles.

3. A method according to claim 1, wherein said pulsed magnetic field is activated to direct the whole of said at least one pulse of said charged particles.

4. A method according to claim 1, wherein said pulsed magnetic field is activated to direct said at least one part of said at least one pulse of said charged particles.

5. A method according to claim 4, wherein said at least one part of said at least one pulse of said charged particles is a part having said preselected range of particle energy.

6. The method of claim 5, wherein said at least one electromagnet is positioned at such a distance from said target that the energy dispersion of said particles in said at least one pulse is sufficient that said preselected range of particle energy can be resolved temporally by the response time of said at least one electromagnet and its current feed.

7. A method according to claim 4, wherein said pulsed magnetic field directs particles having said preselected range of particle energy away from other particles in said at least one pulse.

8. A method according to claim 4, wherein said pulsed magnetic field is activated during that portion of said at least one laser pulse predetermined such that said pulsed magnetic field diverts said part of said at least one pulse having said preselected range of particle energy.

9. The method of claim 1, wherein said light obtained from said laser pulses is passed through an optical delay element, so as to control the time at which said illumination is applied to said light activated switch.

10. A method of selecting charged particles having a predetermined energy range, from a pulse of charged particles generated by impact of a laser pulse a target, said method comprising:
    supplying current from an optically switched source to at least one electromagnet generating a magnetic field disposed such that when activated, said charged particles are diverted from their original path; and
    switching said at least one magnetic field in synchronization with said laser pulse for a predetermined time period, such that that part of said pulse of charged particles comprising particles of the energy range to be selected, is diverted by said at least one magnetic field.

11. A method according to claim 10, wherein said magnetic field is disposed at a distance from said target such that the energy dispersion of said particles in said at least one pulse is sufficient that particles of said energy range to be selected, can be resolved temporally.

12. A method according to claim 10, wherein said at least one magnetic field is activated from the beginning of said predetermined time period to the end of said predetermined time period.

13. A method according to claim 10, wherein said predetermined time period is selected by use of a variable optical delay line.

14. A system for selecting charged particles having a predetermined range of energies, from a pulse of charged particles having a range of energies, comprising:
- a first electromagnet and a second electromagnet in mutual proximity, such that when either of said electromagnets is activated, said charged particles are diverted from their original path; and
- a control system adapted to activate said first electromagnet to produce a first magnetic field pulse commencing at the moment in time when it is desired that said first magnetic pulse field commence diversion of said pulse train of charged particles at one end of said predetermined range of energies, and to activate said second electromagnet to produce a second magnetic field pulse in the reverse direction at the moment in time when it is desired that said second magnetic pulse field terminate diversion of said charged particles at the other end of said predetermined range of energies.

15. The system of claim 14 wherein said predetermined range of energies is delineated by the moments in time defined by the leading edges of said first and second magnetic field pulses.

16. The system of claim 14 wherein said pulse of charged particles is generated by impact of a laser pulse on a target, said system further comprising optical control switches for switching currents producing said first and second magnetic field pulses.

17. A method of selecting charged particles having a predetermined range of energies, from a pulse of charged particles having a range of energies, comprising:
- providing a first magnetic field pulse and a second magnetic field pulse in mutual proximity, such that when either of said magnetic field pulses are applied to said pulse train of charged particles, said charged particles are diverted from their original path; and
- applying said first magnetic field pulse to define the moment in time when it is desired that said first magnetic pulse field commence diversion of said pulse train of charged particles at one end of said predetermined range of energies, and applying said second magnetic field pulse in the reverse direction to define the moment in time when it is desired that said second magnetic pulse field terminate diversion of said charged particles at the other end of said predetermined range of energies.

18. The method of claim 17 wherein said predetermined range of energies is delineated by the moments in time defined by the leading edges of said first and second magnetic field pulses.

19. The method of claim 17 wherein said pulse train of charged particles is generated by impact of a laser pulse on a target, and said first and second magnetic field pulses are switched by optical control on currents activating said first and second magnetic field pulses.

* * * * *